United States Patent [19]

Baumann et al.

[11] Patent Number: 5,011,971
[45] Date of Patent: Apr. 30, 1991

[54] PROCESS FOR THE PREPARATION OF SUBSTITUTED 3-AMINO-2 (BENZOYL)-ACRYLIC ACID ESTERS, AND A PROCESS FOR THE PREPARATION OF INTERMEDIATES FOR ANTIBACTERIAL ACTIVE COMPOUNDS FROM THESE COMPOUNDS

[75] Inventors: Karl Baumann, Wien; Klaus Fitzinger, Freistadt, both of Austria

[73] Assignee: Chemie Linz Gesellschaft m.b.H., Linz, Austria

[21] Appl. No.: 363,198

[22] Filed: Jun. 8, 1989

[30] Foreign Application Priority Data

Jun. 9, 1988 [AT] Austria ............................. 1495/88

[51] Int. Cl.$^5$ ............................................. C07C 227/04
[52] U.S. Cl. ...................................... 560/38; 546/156
[58] Field of Search ................. 560/38, 39; 564/385; 546/156

[56] References Cited

U.S. PATENT DOCUMENTS 3,054,822  9/1962  Schorr et al. ..................... 560/38
4,003,933  1/1977  Drake ................................. 564/385

FOREIGN PATENT DOCUMENTS 63-316757  12/1988  Japan ................................. 560/39

Primary Examiner—James H. Reamer
Attorney, Agent, or Firm—Wenderoth, Lind & Ponack

[57] ABSTRACT

Process for the preparation of substituted 3-amino-2-(benzoyl)-acrylic acid esters of the formula I

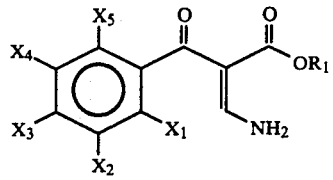

in which $R_1$ denotes an alkyl radical with 1 to 4 C atoms, $X_1$ denotes halogen, in particular fluorine or chlorine, $X_2$, $X_3$, $X_4$ and $X_5$ denote hydrogen, halogen, in particular fluorine or chlorine, an alkyl radical having 1–4 C atoms or an alkoxy radical having 1–4 C atoms in the alkyl chain, by selectively reducing a substituted 2-cyano-3-hydroxy-3(phenyl)acrylic acid ester of the formula II

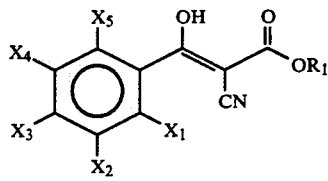

in which $R_1$, $X_1$, $X_2$, $X_3$, $X_4$ and $X_5$ have the meaning given above, and a process for the preparation of intermediate products for antibacterially active compounds from these compounds.

8 Claims, No Drawings

PROCESS FOR THE PREPARATION OF SUBSTITUTED 3-AMINO-2 (BENZOYL)-ACRYLIC ACID ESTERS, AND A PROCESS FOR THE PREPARATION OF INTERMEDIATES FOR ANTIBACTERIAL ACTIVE COMPOUNDS FROM THESE COMPOUNDS

DESCRIPTION

The invention relates to a new process for the preparation of substituted 3-amino-2-(benzoyl)-acrylic acid esters, and a process for the preparation of intermediate products for antibacterially active compounds from these compounds.

3-Aminoacrylic acid esters are known from DE-OS 3,615,767 as starting substances for the preparation of 4-hydroxy-3-quinolinecarboxylic acids. These are obtained from substituted 2-benzoyl-3-alkoxy-acrylic acid esters by replacement of the 3-alkoxy group by a suitable amine. The substituted 2-benzoyl-3-alkoxy-acrylic acid esters are obtained by acylation of monoesters with substituted benzoyl halides to give the corresponding acylmalonic esters, partial acid hydrolysis and decarboxylation to give substituted benzoylacetic acid esters and subsequent condensation with orthoformic acid esters/acetic anhydride. This process comprises 4 reaction stages. Moreover, during the partial hydrolysis and decarboxylation of the acyl esters there is the risk of by-products being formed.

The object of the invention was therefore to provide a simple process which leads, under mild reaction conditions and with excellent yields, to substituted 3-amino-2-(benzoyl)-acrylic acid esters, which are sought after intermediates for the preparation of antibacterially active compounds.

The invention therefore relates to a process for the preparation of substituted 3-amino-2-(benzoyl)-acrylic acid esters of the formula I

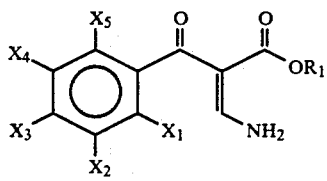

in which $R_1$ denotes an alkyl radical having 1 to 4 C atoms, $X_1$ denotes halogen, in particular fluorine or chlorine, $X_2$, $X_3$, $X_4$ and $X_5$ denote hydrogen, halogen, in particular fluorine or chlorine, an alkyl radical having 1–4 C atoms or an alkoxy radical having 1–4 C atoms in the alkyl chain, comprising selective reduction of a corresponding substituted 2-cyano-3-hydroxy-3(phenyl)-acrylic acid ester of the formula II

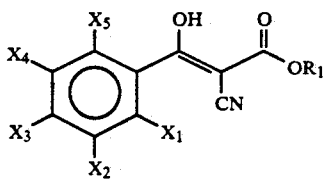

in which $R_1$, $X_1$, $X_2$, $X_3$, $X_4$ and $X_5$ have the abovementioned meaning.

In the formulae I and II, $R_1$ denotes a straight-chain or branched alkyl radical having 1-4 C atoms, for example a methyl, ethyl, propyl, i-propyl, butyl, i-butyl or t-butyl radical. $X_1$ denotes halogen, in particular fluorine or chlorine. $X_2$, $X_3$, $X_4$ and $X_5$ independently of one another can denote hydrogen or halogen, in particular fluorine or chlorine.

The substituents $X_2$, $X_3$, $X_4$ and $X_5$ can furthermore denote a straight-chain or branched alkyl radical having 1–4 C atoms, for example a methyl, ethyl, propyl, i-propyl, butyl, i-butyl or t-butyl radical, or a straight-chain or branched alkoxy radical having 1–4 C atoms in the alkyl chain, for example a methoxy, ethoxy, propoxy or butoxy radical. $X_3$ and $X_4$ independently of one another preferably denote halogen, in particular fluorine or chlorine. $X_2$ and $X_5$ preferably denote hydrogen, halogen, in particular fluorine or chlorine, or a straight-chain or branched alkyl radical having 1–4 C atoms.

The substituted 2-cyano-3-hydroxy-3-(phenyl)-acrylic acid esters of the formula II used as starting compounds for the substituted 3-amino-2-(benzoyl)-acrylic acid esters of the general formula I can be prepared in a manner which is known per se from the corresponding benzoyl halides, in particular the benzoyl chlorides, by condensation with cyanoacetic acid esters.

In this process, the corresponding benzoyl halide is reacted with a cyanoacetic acid ester in the presence of a base, for example sodium hydride or a magnesium alcoholate or sodium alcoholate, in an anhydrous organic solvent, preferably in an aprotic solvent, for example tetrahydrofuran dioxane or diethyl acetate. The reaction solution is then acidified and the reaction product is isolated by extraction and drying.

The compounds of the formula II thus obtained are reduced by the process according to the invention to give the compounds of the formula I.

For this, the corresponding substituted 2-cyano-3-hydroxy-3-(phenyl)-acrylic acid esters are dissolved in a suitable solvent, a hydrogenation catalyst is added and hydrogenation is carried out.

The solvents used are organic solvents which are inert under the reaction conditions, for example methanol, ethanol, dimethylformamide, dioxane, tetrahydrofuran, 1,2-dimethoxyethane or mixtures thereof, or mixtures of these solvents with water.

Palladium-on-active charcoal or Raney nickel are used as catalysts. If $X_1$ and $X_3$ in the formula I both denote chlorine, Raney nickel is preferably used as the catalyst.

The hydrogenation is carried out at temperatures of about 0° to 100° C., preferably at room temperature, depending on the solvent. The hydrogenation can be carried out under normal pressure or under a pressure of about 1 to 5 bar, and is preferably carried out under normal pressure. The reaction time is about 2–5 hours, depending on the substituents, reaction temperature and pressure and catalyst used.

Substituted 3-amino-2-(benzoyl)-acrylic acid esters are useful intermediates for antibacterially active compounds. The compounds obtained by the process described above can be further processed without an extra purification step.

The invention thus furthermore relates to a process for the preparation of intermediate products for antibacterially active compounds of the formula III

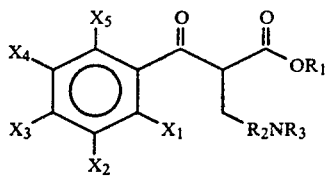

in which $X_2$, $X_3$, $X_4$, $X_5$ and $R_1$ have the meaning given above in formula I, $X_1$ denotes halogen, in particular fluorine or chlorine, $R_2$ denotes H, or $X_1$ and $R_2$ together form a single bond, and $R_3$ denotes H or an alkyl or alkoxy radical which has 1-6 C atoms in the alkyl chain and is optionally substituted by one or more substituents, an optionally substituted cycloalkyl radical having 3-6 C atoms or an aryl or heteroaryl radical which is optionally substituted by one or more substituents, with the proviso that $R_2$ and $R_3$ do not simultaneously denote H, comprising selective reduction of a substituted 2-cyano-3-hydroxy-3-(phenyl)-acrylic acid ester of the formula

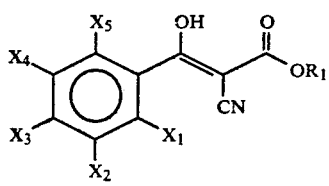

in which $R_1$, $X_1$, $X_2$, $X_3$, $X_4$ and $X_5$ have the meaning given in formula 1, to a substituted 3-amino-2(benzoyl)-acrylic acid ester of the formula I, in which $R_1$, $X_1$, $X_2$, $X_3$, $X_4$ and $X_5$ have the meaning given in claim I, and the compounds of the formula I are then reacted with a compound of the formula $R_3NH_2$      IV in which $R_3$ has the abovementioned meaning, if appropriate in the presence of an acid and in the presence of a solvent.

The reaction of the substituted 3-amino-2-(benzoyl)-acrylic acid esters is carried out, if appropriate, in the presence of an acid, depending on the nucleophilicity of the corresponding amine, for example in the presence of trifluoroacetic acid, p-toluenesulphonic acid or acetic acid. Examples of solvents which are used are dioxane, tetrahydrofuran, acetonitrile, dimethylformamide, 1,2-dimethoxyethane, chloroform, methyl chloride, N-methylpyrrolidone and dimethylacetamide. The reaction can be carried out at temperatures of about 0°–150° C., preferably 0°–80° C.

EXAMPLE 1

Methyl 2-cyano-3-hydroxy-3-(2,4,5-trifluorophenyl)-acrylate 26.92 g of a 55% dispersion of sodium hydride in white oil was suspended in 200 ml of absolute tetrahydrofuran, the suspension was cooled to 5° C. and a solution of 32.06 g of methyl cyanoacetate in 60 ml of absolute tetrahydrofuran was added dropwise so that a temperature interval of 10°–15° C. was maintained. When the addition had ended, the mixture was subsequently stirred at about 10° C. for 20 minutes and a solution of 60 g of 2,4,5-trifluorobenzoyl chloride in 60 ml of absolute tetrahydrofuran was then added dropwise so that 15° C. was not exceeded. The mixture was then subsequently stirred at about 5° C. for a further hour and thereafter poured onto 400 ml of 4N HCl/400 g of ice and the product was extracted with methylene chloride. The organic phase was dried over sodium sulphate and the volatile constituents were stripped off on a rotary evaporator. The crystalline evaporation residue was recrystallized from methanol/ethyl acetate.

75 g (94.2% of theory) of colourless crystals, Melting point: 125°–127° C. (MeOH/ethyl acetate).

EXAMPLE 2

Methyl 2-cyano-3-(2-chloro-4,5-difluorophenyl)-3-hydroxyacrylate

The preparation was carried out analogously to Example 1. 13.91 g of 2-chloro-4,5-difluorobenzoyl chloride were used as the starting compound.

14.35 g (79.6% of theory) of beige crystals, Melting point: 169°–71° C. (ethyl acetate).

EXAMPLE 3

Methyl 2-cyano-3-(2,4-dichloro-5-fluorophenyl)-3-hydroxyacrylate

The preparation was carried out analogously to Example 1. 15 g of 2,4-dichloro-5-fluorobenzoyl chloride were used as the starting compound.

16.47 g (86.1% of theory) of beige crystals, Melting point: 168°–171° C. (ethyl acetate).

EXAMPLE 4

Methyl 3-amino-2-(2,4,5-trifluorobenzoyl)-acrylate 29 g of the product from Example 1 were dissolved in 2,000 ml of ethanol, 3 g of 10% strength palladium-on-active charcoal were added, the mixture was degassed and hydrogenation was carried out under normal pressure at room temperature for three hours. The catalyst was filtered off, the filtrate was evaporated and the residue was recrystallized from benzene.

25.11 g (85.3% of theory) of pale green crystals, Melting point: 125°–127° C. (benzene).

EXAMPLE 5

Methyl 3-amino-2-(2-chloro-4,5-difluorobenzoyl)acrylate

The preparation was carried out analogously to Example 4. 12 g of the product from Example 2 were used as the starting compound.

10.5 g (86.9% of theory) of beige crystals, Melting point: 139°–143° C. (i-propanol) decomposition.

EXAMPLE 6

Methyl 3-amino-2-(2-chloro-4,5-difluorobenzoyl)acrylate 1.0 g of the product from Example 2 was dissolved in methanol, 0.5 g of Raney nickel was added and hydrogenation was carried out under normal pressure at room temperature for four hours. The catalyst was separated off, the solution which remained was evaporated and the evaporation residue was recrystallized from i-propanol.

0.71 g (70.3% of theory) of beige crystals Melting point: 139°–143° C. (i-propanol) decomposition.

EXAMPLE 7

Methyl 3-amino-2-(2,4-dichloro-5-fluorobenzoyl)acrylate

The preparation was carried out analogously to Example 6. 4 g of the product from Example 3 were used as the starting compound.

3.42 g (84.9% of theory) of colourless crystals, Melting point: 112°–115° C. (petroleum ether).

EXAMPLE 8

Methyl 3-cyclopropylamino-2-(2-chloro-4,5-difluorobenzoyl)acrylate 2 g of the product from Example 5 and 0.62 g of cyclopropylamine were stirred in 30 ml of dry acetonitrile at room temperature for 30 minutes. The volatile constituents were then stripped off on a rotary evaporator and the evaporation residue was recrystallized from ether.

1.77 g (77.3% of theory) of colourless crystals Melting point: 119°–121° C. (diethyl ether) decomposition.

EXAMPLE 9

Methyl 3-cyclopropylamino-2-(2,4,5-trifluorobenzoyl)acrylate

The preparation was carried out analogously to Example 8. 1 g of the product from Example 4 was used as the starting compound.

1.05 g (90.9% of theory) of colourless crystals, Melting point: 124°–127° C. (ether/petroleum ether).

EXAMPLE 10

Methyl 3-((2,4-difluorophenyl)amino)-2-(2,4,5-trifluorobenzoyl)acrylate

A mixture consisting of 1 g of the product from Example 4, 0.88 g (1.2 equivalents) of p-toluenesulphonic acid monohydrate and 1.25 g (2.5 equivalents) of 2,4-difluoroaniline in 20 ml of dry acetonitrile was heated under reflux for one hour. After cooling, the mixture was diluted with ethyl acetate, washed twice with N HCl and once with sodium chloride solution, dried over sodium sulphate, filtered and evaporated. The evaporation residue was recrystallized from ether.

0.95 g (69.8% of theory) of colourless crystals, Melting point: 116°–119° C. (ether).

EXAMPLE 11

Methyl 2-(2-chloro-4,5-difluorobenzoyl)-3-((4-fluorophenyl)amino)acrylate

The preparation was carried out analogously to Example 10 with 1.0 g of the product from Example 5, 1.01 g of p-fluoroaniline and 0.69 g of p-toluenesulphonic acid.H₂O.

0.82 g (61.2% of theory) of colourless crystals, Melting point: 98°–103° C. (diethyl ether/petroleum ether) decomposition.

EXAMPLE 12

Methyl 6,7-difluoro-1,4-dihydro-4-oxo-quinoline-3-carboxylate 5 g of the product from Example 4 were taken up in 40 ml of dioxane, 0.93 g of sodium hydride (55% strength in white oil) was added and the mixture was first stirred at room temperature for 30 minutes and then heated under reflux for 45 minutes. After cooling, it was poured onto 150 ml of N HCl and the solid obtained was filtered off and recrystallized from acetone.

2.91 g (63.1% of theory) of pale beige crystals, Melting point: from 250° C. sublimation, from 307° C. decomposition (acetone).

EXAMPLE 13

Methyl 6,7-difluoro-1,4-dihydro-1-methoxy-4-oxo-quinoline-3-carboxylate

A mixture consisting of 1.0 g of the product from Example 4 and 0.35 g of O-methylhydroxylamine hydrochloride in 25 ml of dry acetonitrile was heated under reflux for four hours. It was then diluted with ethyl acetate, washed with N HCl and water, dried over sodium sulphate, filtered and evaporated. The crystalline evaporation residue was recrystallized from acetonitrile.

0.70 g (67.3% of theory) of beige crystals, Melting point: 205°–208° C. (acetonitrile).

EXAMPLE 14

Methyl 3-cyclopropylamino-2-(2,4-dichloro-5-fluorobenzoyl)acrylate

The preparation was carried out analogously to Example 8. 1.0 g of the product from Example 7 was used as the starting compound.

0.72 g (63.3% of theory) of colourless crystals Melting point: 156°–158° C. (ethyl acetate/ether) decomposition.

EXAMPLE 15

Methyl 3-((2,4-difluorophenyl)amino)-2-(2,4,5-trifluorobenzoyl)acrylate 26.92 g of a 55% strength dispersion of sodium hydride in white oil were suspended in 200 ml of absolute tetrahydrofuran, the suspension was cooled to 5° C. and a solution of 32.06 g of methyl cyanoacetate in 60 ml of absolute tetrahydrofuran was added dropwise so that a temperature interval of 10°–15° C. was maintained. When the addition had ended, the mixture was subsequently stirred at about 10° C. for 20 minutes and a solution of 60 g of 2,4,5-trifluorobenzoyl chloride in 60 ml of absolute tetrahydrofuran was then added dropwise so that 15° C. was not exceeded. The mixture was then subsequently stirred at about 5° C. for a further hour and thereafter poured onto 400 ml of 4N HCl/400 g of ice and the product was extracted with methylene chloride. The organic phase was dried over sodium sulphate and the volatile constituents were stripped off on a rotary evaporator.

The evaporation residue was dissolved in methanol, 3 g of 10% strength palladium-on-active charcoal were added, the mixture was degassed and hydrogenation was carried out under normal pressure at room temperature for three hours. The catalyst was filtered off, 70.22 g of p-toluenesulphonic acid monohydrate and 100 g of 2,4-difluoroaniline were added to the filtrate and the mixture was heated under reflux for one hour.

The mixture was then concentrated on a rotary evaporator and the residue was partitioned between 1N HCl and ethyl acetate.

The organic phase was washed with sodium chloride solution, dried over sodium sulphate and evaporated.

The evaporation residue was recrystallized from ether.

68 g (60% of theory) of colourless crystals. Melting point 116°–119° C. (ether).

What we claim is:

1. A process for the preparation of a substituted 3-amino-2-(benzoyl)-acrylic acid ester of the formula I

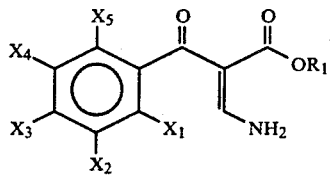

in which $R_1$ denotes an alkyl radical having 1 to 4 C atoms, $X_1$ denotes halogen, and $X_2$, $X_3$, $X_4$ and $X_5$ denote hydrogen or halogen, comprising selectively reducing, with hydrogen in the presence of a hydrogenation catalyst in a solvent or diluent, a corresponding substituted 2-cyano-3-hydroxy-3-hydroxy-3(phenyl)-acrylic acid ester of the formula II

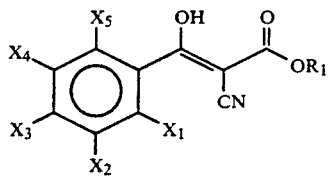

in which $R_1$, $X_1$, $X_2$, $X_3$, $X_4$ and $X_5$ are as defined above.

2. A process according to claim 1 wherein palladium-on-active charcoal or Raney nickel is employed as the hydrogenation catalyst.

3. A process according to claim 1 wherein the solvent or diluent is methanol, ethanol, tetrahydrofuran, dioxane, dimethylformamide, 1,2-dimethoxyethane or mixtures thereof or mixtures with water.

4. A process according to claim 1 wherein the hydrogenation is carried out under normal pressure at room temperature.

5. A process according to claim 1 wherein $R_1$ denotes an alkyl radical having 1 to 4 C atoms, $X_1$, $X_3$ and $X_4$ denote halogen, and $X_2$ and $X_5$ denote hydrogen or halogen.

6. A process according to claim 1 wherein $X_1$ is fluorine or chlorine.

7. A process according to claim 5 wherein $X_1$, $X_3$ and $X_4$ are fluorine or chlorine and $X_2$ and $X_5$ are hydrogen, fluorine or chlorine.

8. A process for the preparation of an intermediate product for an antibacterially active compound of the formula

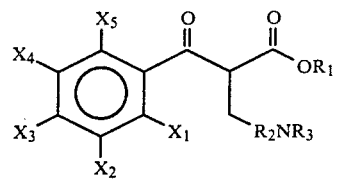

in which $R_1$ denotes an alkyl radical having 1 to 4 carbon atoms, $X_2$, $X_3$, $X_4$ and $X_5$ denote hydrogen or halogen, $X_1$ denotes halogen, $R_2$ denotes H, or $X_1$ and $R_2$ together form a single bond, and $R_3$ denotes H or an alkyl or alkoxy radical which has 1–6 C atoms in the alkyl chain, a cycloalkyl radical having 3–6 C atoms or an aryl radical which is optionally substituted by one or more halogens, with the proviso that $R_2$ and $R_3$ do not simultaneously denote H, comprising selectively reducing, with hydrogen in the presence of a hydrogenation catalyst in a solvent or diluent, a substituted 2-cyano-3-hydroxy-3-(phenyl)-acrylic acid ester of the formula II

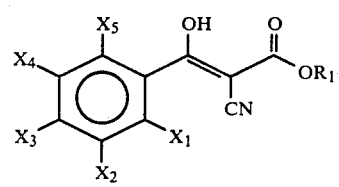

in which $R_1$, $X_1$, $X_2$, $X_3$, $X_4$ and $X_5$ are as defined above to yield a substituted 3-amino-2(benzoyl)-acrylic acid ester of the formula I

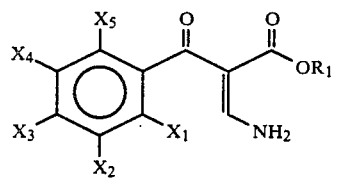

in which $R_1$, $X_1$, $X_2$, $X_3$, $X_4$ and $X_5$ are as defined above and reaching the compound of the formula I in the presence of a solvent with a compound of the formula IV $R_3NH_2$        IV in which $R_3$ denotes
  (a) an alkyl radical with 1–6 C atoms, or a cycloalkyl radical with 3–6 C atoms, whereby the corresponding N-substituted amines of the formula III, in which $R_2$ denotes H, are obtained, or
  (b) an aryl radical which is unsubstituted or is substituted by one or more halogens, the reaction being performed in the presence of an acid, whereby the corresponding N-substituted amines of the formula III, in which $R_2$ denotes H, are obtained, or
  (c) an alkoxy radical which has 1–6 C atoms, whereby an N-substituted quinoline carboxylate of the formula III, in which $R_2$ and $X_1$ together form a single bond, are obtained, wherein the products obtained according to (a) and (b) above can then be further reacted in the presence of a base to form the corresponding N-substituted quinoline carboxylates of the formula III, in which $R_2$ and $X_1$ together form a single bond.

* * * * *